United States Patent [19]

Isaacson

[11] Patent Number: 5,205,721
[45] Date of Patent: Apr. 27, 1993

[54] SPLIT STATOR FOR MOTOR/BLOOD PUMP

[75] Inventor: Milton S. Isaacson, Dayton, Ohio

[73] Assignee: Nu-Tech Industries, Inc., Dayton, Ohio

[21] Appl. No.: 654,833

[22] Filed: Feb. 13, 1991

[51] Int. Cl.$^5$ .............................................. F04B 35/04
[52] U.S. Cl. .................................. 417/356; 417/423.1; 417/423.7; 310/184; 310/254
[58] Field of Search ............... 417/348, 350, 355, 356, 417/423.1, 423.7; 310/178, 180, 184, 254

[56] References Cited

U.S. PATENT DOCUMENTS

| | | | |
|---|---|---|---|
| 2,424,299 | 7/1947 | Baudry et al. | 310/258 |
| 3,426,224 | 2/1969 | Esters | 310/51 |
| 3,426,226 | 2/1969 | Frank | 310/162 |
| 3,584,458 | 6/1971 | Wetzler | 60/39.02 |
| 3,608,088 | 9/1971 | Dorman et al. | 623/3 |
| 3,938,913 | 12/1972 | Isenberg et al. | 417/356 |
| 4,135,253 | 1/1979 | Reich et al. | 3/1.7 |
| 4,217,510 | 8/1980 | Detinko et al. | 310/51 |
| 4,263,524 | 4/1981 | Diederichs | 310/112 |
| 4,332,133 | 6/1982 | Schwarz et al. | 415/115 |
| 4,382,199 | 5/1983 | Isaacson | 310/87 |
| 4,416,111 | 11/1983 | Lenahan et al. | 60/39.29 |
| 4,487,016 | 12/1984 | Schwarz et al. | 60/39.75 |
| 4,513,567 | 4/1985 | Deveau et al. | 60/39.02 |
| 4,594,522 | 6/1986 | Fujiwara et al. | 310/42 |
| 4,594,523 | 8/1984 | Horita et al. | 310/42 |
| 4,604,541 | 8/1986 | Murasato et al. | 310/180 |
| 4,625,712 | 12/1986 | Wampler | 128/1 |
| 4,688,998 | 8/1987 | Olsen et al. | 417/356 |
| 4,704,121 | 11/1987 | Moise | 623/3 |
| 4,779,614 | 10/1988 | Moise | 600/16 |
| 4,815,272 | 3/1989 | Laurello | 60/39.75 |
| 4,817,586 | 4/1989 | Wampler | 600/16 |
| 4,846,152 | 7/1989 | Wampler et al. | 600/16 |
| 4,893,983 | 1/1990 | McGeehan | 60/39.24 |
| 4,895,557 | 1/1990 | Moise et al. | 600/16 |
| 4,901,520 | 2/1990 | Kozak et al. | 60/39.02 |
| 4,906,229 | 3/1990 | Wampler | 600/16 |
| 4,908,012 | 3/1990 | Moise et al. | 600/16 |
| 4,912,831 | 4/1990 | Levino | 29/596 |
| 4,939,400 | 7/1990 | Matsushita et al. | 310/208 |
| 4,944,722 | 7/1990 | Carriker et al. | 600/16 |
| 4,957,504 | 9/1990 | Chardack | 623/3 |
| 4,968,911 | 11/1990 | Denk | 310/42 |
| 5,022,817 | 6/1991 | O'Halloran | 415/115 |

OTHER PUBLICATIONS

Kaga et al., "Synchronous Machine", Tokyo Denki University, Dec. 20, 1967 pp. 374–375.

Primary Examiner—Richard A. Bertsch
Assistant Examiner—Charles Freay
Attorney, Agent, or Firm—Wood, Herron & Evans

[57] ABSTRACT

A motor/blood pump which axially pumps blood to a patient connected to a heart/lung machine includes a cylindrical pump housing, a rotor located in the housing, at least one impeller blade attached to the rotor, a pair of stator halves mechanically connectable to the outside of the housing and a motor controller electrically connected to the stator halves. The controller electrically actuates the interconnected stator halves to rotatably drive the rotor on a hydrodynamic bearing of the blood in the housing, and the impeller blade axially pumps blood through the housing. Mechanically and electrically interconnectable stator halves enable the reusable stator to be connected to and disconnected from the disposable pump housing without interrupting the blood flow path.

20 Claims, 2 Drawing Sheets

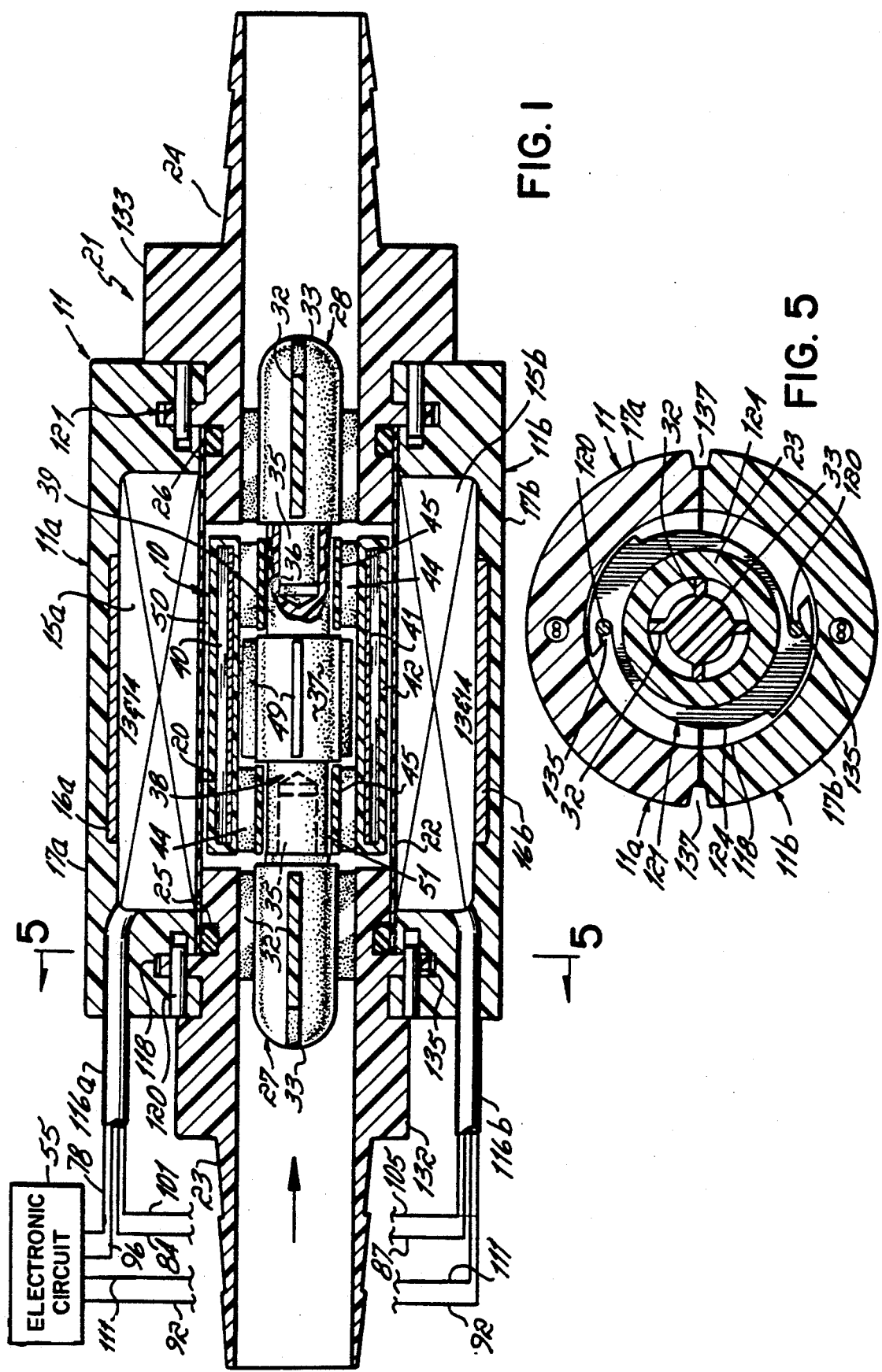

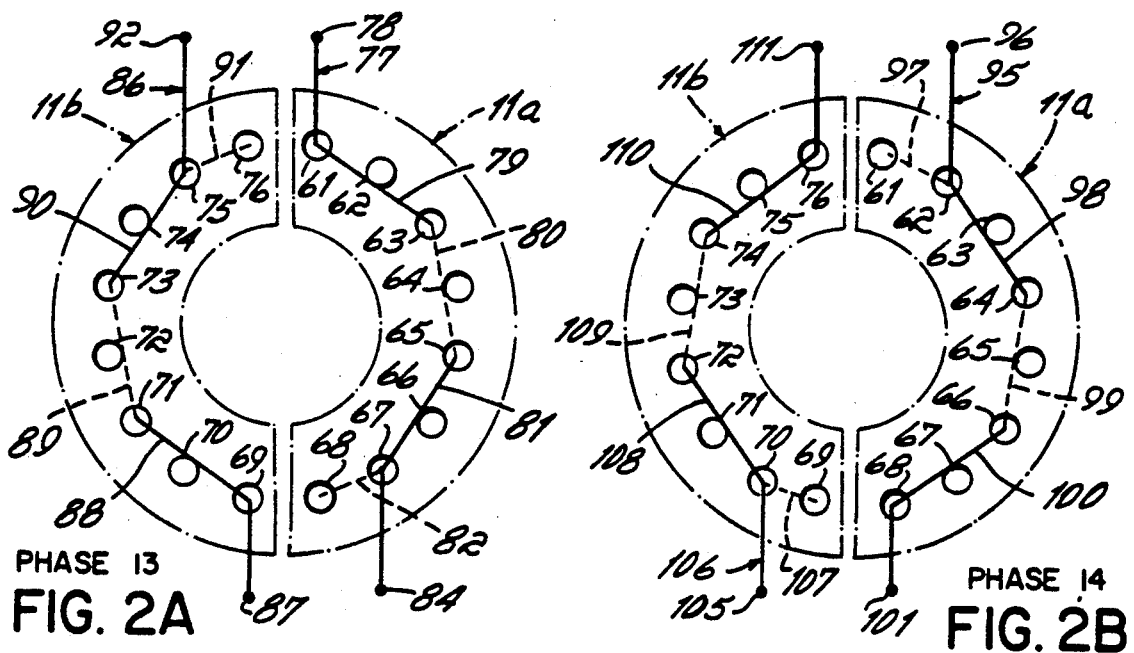
PHASE 13
FIG. 2A
PHASE 14
FIG. 2B
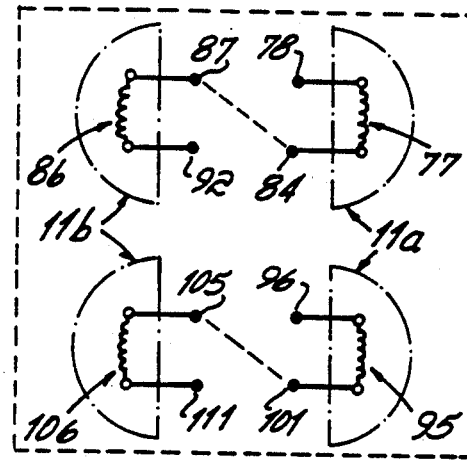
FIG. 3
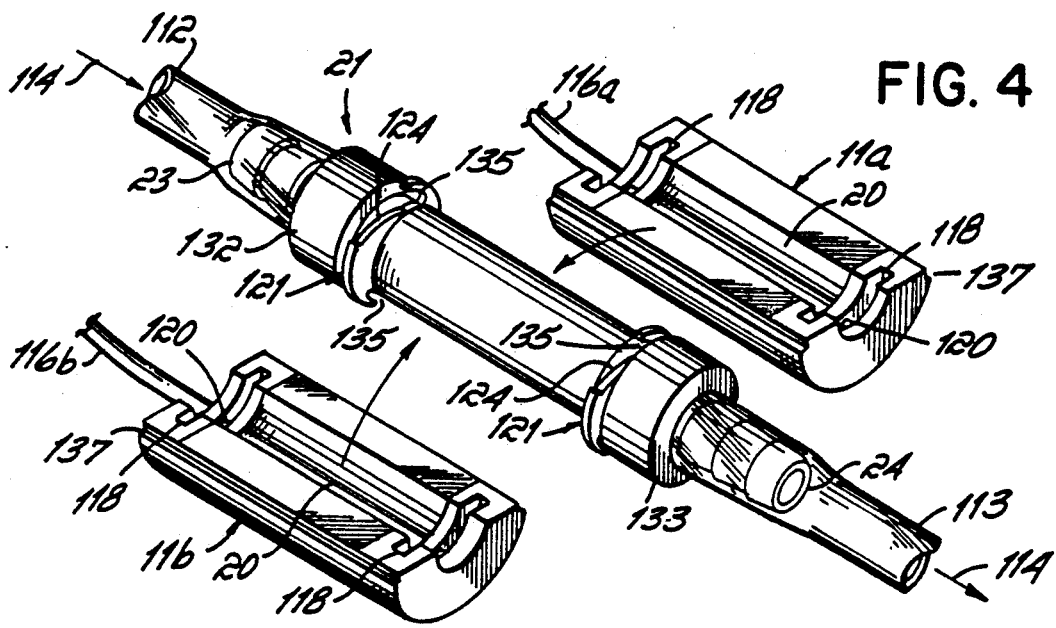
FIG. 4

SPLIT STATOR FOR MOTOR/BLOOD PUMP

FIELD OF THE INVENTION

This invention relates to a split stator for a motor that drives an axial flow blood pump in a heart/lung machine.

BACKGROUND OF THE INVENTION

When interconnected to the circulatory system of a patient, a heart/lung machine oxygenates, pumps and heats the blood supply of a patient. Oxygen poor blood flows from the patient to the heart/lung machine, where it is oxygenated and heated, and then pumped back to the patient. Essentially, the pump used in a heart/lung machine serves as a temporary heart for the patient. Prior to connection of a patient to a heart/lung machine, it is necessary to prime the pump with blood compatible saline.

In the past, several types of pumps have been used to pump blood through a heart/lung machine. For instance, positive displacement peristaltic pumps and centrifugal pumps have been used for this purpose. Both of these pump types require a relatively large volume of saline for priming.

Applicant's co-pending U.S. patent application Ser. No. 07/529,598, filed on May 29, 1990, discloses an axial flow motor/blood pump. This motor/blood pump requires significantly less saline solution for priming. This axial motor/blood pump also has fewer parts and is less expensive than prior pumps, both of which features are particularly important because blood-contacting medical equipment is thrown away after a single use. Disposing of equipment or components that directly contact the blood reduces the risk of transmitting blood carried diseases or viruses such as the HIV virus which carries acquired immuno-deficiency syndrome ("AIDS").

With this axial flow motor/blood pump, the motor controller and stator are reused, while the pump and its components are thrown away after a single use. The pump includes a housing connected in line with the blood flow path. To connect the pump to the blood flow path, tubes are connected to the ends of the housing. Prior to connection of the tube at one end of the housing, the stator is slid over that end of the housing and then the tube is connected. The tubes and the housing are normally sterilized when packaged by the manufacturer. However, because a nonsterilized piece of equipment, i.e., the stator, is slid over the end of the housing, the assembled motor/blood pump must be sterilized again prior to use. After use, one of the tubes is disconnected from the housing, and the stator is slidably removed from the housing for reuse, while the housing and tubing are discarded.

Although this axial flow motor/blood pump has proved to be advantageous over prior blood pumps, applicant has recognized that a further advantage could be achieved if the reusable components of the motor/blood pump could be connected/disconnected to/from the disposable components without interrupting the blood flow path. This would eliminate the need to resterilize components prior to use, and it would also reduce the amount of direct blood contact required of hospital personnel when disconnecting a patient from a heart/lung machine.

SUMMARY OF THE INVENTION

To this end, this invention contemplates a motor/blood pump that utilizes a disposable pump housing which houses a rotor, and a pair of reusable stator halves connectable to the outside of the housing and adapted to rotatably drive the rotor to pump blood axially through the housing.

Because the motor for this axial flow motor/blood pump uses two separate stator halves which readily connect to a disposable housing for an axial pump that resides in the blood flow path, this invention eliminates the need to interrupt the blood flow path when connecting a patient to a heart/lung machine. Easy connection of the stator halves eliminates the prior need to resterilize components after interrupting the blood flow path to slide a cylindrical stator onto the disposable pump housing. Because the stator halves may also be readily disconnected from the disposable pump housing when the patient no longer needs the heart/lung machine, this invention also eliminates unnecessary, direct contact with the patient's blood.

According to a preferred embodiment of the invention, a motor/blood pump includes a cylindrical pump housing, a pair of spaced end mounting components integral with the outside of the housing, a rotor located in the housing, at least one impeller blade attached to the rotor, a pair of epoxy-encapsulated stator halves connectable to the mounting components on the outside of the housing and a motor controller electrically connected to the stator halves. Each stator half mechanically connects to the housing via the spaced stator mounting components to form a cylindrical stator around the housing.

The stator halves are then electrically connected to each other and to the controller externally of the cylindrical shell formed by the mechanically interconnected stator halves. The controller electrically actuates the stator halves to set up a rotating magnetic field which rotatably drives the rotor and impeller blade. The rotor rotates within the housing on a hydrodynamic bearing formed by the fluid being pumped, and the impeller blades axially pump the liquid through the housing. The simple mechanical connections of the stator halves to the disposable housing and the external electrical connections of the stator halves to each other and the controller enable easy connection/disconnection of the reusable stator to/from the disposable axial flow pump, without requiring an interruption of the blood flow path.

To mechanically interconnect the stator halves, each of the two mounting components serves as a bearing surface for the stator halves and includes a pair of oppositely directed, declined cam surfaces that terminate in a cam end. By oppositely directed, it is meant that the cam surfaces and cam ends are angularly spaced 180° apart, or face radially outward in opposite directions. Each stator half has a pair of correspondingly spaced cam followers adapted to coact with one spaced pair of cam surfaces and cam ends. Preferably, the cam followers are pins embedded in the epoxy-encapsulation of the respective stator half, and each pin is located within a radially extending groove formed in the epoxy during encapsulation.

Both of the motor stator halves are connected in the same fashion to the pump housing, on opposite sides. To mount the stator, the grooves of one of the stator halves are located over the mounting components, and the pins are placed in engagement with the declined cam surfaces. The other stator half is then positioned in the same manner, against the declined cam surfaces on the opposite side of the pump housing. Then, by gripping the housing outside of the cams and rotating the stator halves with respect to the housing, the four pins of the stator halves rotate within the cams and eventually lock into position within the cam ends. To separate the stator halves from the housing and rotor, the stator halves are simply rotated in the other direction with respect to the housing and mounting components.

This mechanical connection properly aligns the two halves of the motor stator with respect to each other and with respect to the rotor, while positively locking all three of the components into position. As a further advantage, this camming action for disconnection of the stator halves effectively overcomes the magnetic attraction between the rotor and the stator in the case of a permanent magnet rotor, and/or the friction present in tightly fitting bearing mountings, without requiring additional tools that might otherwise damage the components. Finally, this locking mechanism does not add substantially to the length of the motor stator and rotor configuration, and the outside diameter of the stator and rotor configuration remains unaltered.

To split the motor stator electrically without incurring a significant loss of performance or inconvenience in connecting multiple conductors, this invention utilizes a unique winding and electrical connection scheme. Although a motor stator can consist of more than three phases, the typical motor stator consists of either two or three phrases, each phase consisting of a continuous electrical conductor. Within each phase the continuous electrical conductor is wound to form multiple coils in slots of the motor stator. The coils of one phase typically overlap the coils of the other phase(s), and the coils of one phase typically are displaced with respect to the other phase(s). Thus, a severing of a typical motor in half would require cutting through a multiple number of coils and interrupting the continuity of the electrical windings.

According to this invention, each phase is wound by two separate electrical conductors, one for each stator half. The two conductors are then connected externally of the facially engaged, epoxy-encapsulated stator halves, thereby avoiding the necessity to extend the electrical line between the slots located along the parting plane between the two stator halves. Thus, for two phases, with two stator halves, the coils are formed from four electrical conductors. Each conductor either has a coil of shortened pitch, or a coil is eliminated, to avoid crossing the parting plane between the two stator halves. No coils cross the parting plane between the stator halves.

In further embodiments of the invention, either additional turns or an additional, parallel coil could be added to each of the short pitched coils to compensate for the reduced magnetic flux at the short pitched coils.

In addition to blood pump applications, this invention applies to a variety of other pump applications where it may be desirable to use an axial pump as a disposable item, separate from a reusable motor stator. For instance, in some cases it may be desirable to avoid operator contact with the fluid being pumped. The motor/pump of this invention allows the components contacting the fluid to be disconnected and discarded, without requiring any contact.

This invention also relates to other applications for motors wherein it is either impossible or undesirable to introduce the rotor axially into the motor stator or armature bore. This configurational problem is generally encountered when the rotor shaft must terminate in a larger diameter on both ends of the shaft, or where the rotor shaft must be pre-assembled to larger diameter components on both ends.

For these cases, this invention eliminates the need to axially introduce the rotor into the bore. Instead, the rotor can be placed first into one half of the motor sator, and then the second half of the motor stator can be closed over the rotor. The two halves of the motor stator are subsequently connected, both mechanically and electrically. Alternately, a pair of spaced mounting components with opposing cam surfaces and cam ends could be carrie don the rotor shaft, with each stator half connectable to the spaced mounting components.

These and other features of the invention will be more readily appreciated in view of the following detailed description and the drawings.

BRIEF DESCRIPTION OF THE DRAWINGS

FIG. 1 is a diagrammatic longitudinal cross-sectional view through the center of a motor blood/pump in accordance with a preferred embodiment of the invention.

FIGS. 2A and 2B are cross-sectional schematic views of the motor/blood pump shown in FIG. 1, with a first phase of motor windings shown schematically in FIG. 2A, and a second phase of motor windings shown schematically in FIG. 2B.

FIG. 3 is a schematic depicting the electrical connections for the motor windings shown in FIGS. 2A and 2B.

FIG. 4 is a perspective view of the motor/blood pump prior to connection of the stator halves to the blood pump.

FIG. 5 is a cross section taken along lines 5—5 of FIG. 4.

DETAILED DESCRIPTION OF THE DRAWINGS

Referring to FIG. 1 of the drawings, a rotor 10 is supported in a stator, designated generally by numeral 11. The stator 11 comprises two epoxy-encapsulated stator halves 11a and 11b, each of which has two phase windings 13 and 14 wound on respective magnetizable core laminations 15a and 15b which have been "halved" to accommodate the half stators 11a and 11b, respectively. Each stator half, 11a or 11b, further includes a metal yoke half 16a or 16b, which surrounds the respective cores 15a or 15b, and a layer of plastic or epoxy encapsulation 17a or 17b, which surrounds the respective metal yoke halves. The encapsulation is preferably epoxy although any one of a number of plastics would also work. Together, the stator halves 11a and 11b form a stator 11, or stator assembly, with an internal, cylindrically shaped bore 20 extending therethrough. The details of the connections between the stator halves 11a and 11b are described later in the application.

A plastic pump housing generally referred to as housing assembly 21, includes an interior sleeve 22 with exterior sections 23 and 24 inserted into outer ends of the sleeve 22 and recessed O-rings 25 and 26, seated adjacent the inner ends of exterior sections 23 and 24, respectively. Section 23 is located at the fluid inlet end of pump housing 21, and section 24 is located at the fluid outlet end. Presently, sleeve 22 and sections 23 and 24 are machined to the desired shapes. However, it would also be possible to mold these components. Ultimately, it may also be possible to eliminate the O-rings with snap action or laser welding of these three separate components as one piece. The components of the plastic housing assembly 21 are preferably a thermoplastic polyurethane (ISOPLAST 301 by Dow Chemical).

Sections 23 and 24 have fluted outer ends onto which tubes (shown in FIG. 4) are connected. Together, the tubes and the housing 21 form a blood flow path that conveys blood to a patient from a heart/lung machine. If desired, two pumps may be used, in which case two housing assemblies 21 would be connected in series along the blood flow path.

Each of the exterior sections 23 and 24 has a pump stator support ring 27 or 28, respectively, inserted into an inner end prior to connection to sleeve 22. Each pump stator support ring has four radial pump stator vanes 32 that interconnect radially with a rounded, central portion 33. Each central portion 33 has a stud 35 that axially seats within a recess 36 in a member that extends axially from a center hub 37 located inside sleeve 22. The members are designated 38 and 39 for the inlet and outlet ends of the pump housing 21, respectively. When interconnected between the stator support rings 27 and 28, the hub 37 locates the rotor 10 within the sleeve 22.

The rotor 10 is actually a rotor assembly with eight axially-extending pole pieces 40 and a back iron ring 41 that are embedded in a cylinder of polyurethane plastic resin 42. The rotor 10 has two sets of impeller blades 44 that are axially spaced from each other. The impeller blades 44 have radially inner ends mounted on a hub support cylinder 45 and radially outer ends embedded in the plastic cylinder 42. The hub support cylinders 45 are located radially externally of the members 38 and 39. Intermediate stator vanes 49 are mounted on the hub 37 and project into the space between the two sets of impeller blades 44. In sum, the pump has three sets of stator blades, located at the inlet, i.e., on support ring 27, at the outlet, i.e., on support 28, and intermediate, i.e., vanes 49. A cylindrical gap 50 is created between the cylindrical housing assembly 21 and the plastic cylinder 42 of the rotor 10. The gap 50 is preferably about 0.0035" in radial dimension. An inner gap 51 is formed between each hub support cylinder 45 and a respective extender 38 or 39. The gap 51 is preferably about 0.0045" in radial dimension. As explained in applicant's co-pending U.S. application Ser. No. 07/529,598, filed on May 29, 1990, and which is expressly incorporated by reference herein in its entirety, the motion of the rotor 10 within these gaps provides a pressure distribution on the rotor 10, thereby creating hydrodynamic bearings that maintain the rotor 10 substantially centered radially in the stator 11. The axial length of gap 50 is about 1". The axial length of the gap 51 is about 0.3". The inside diameter of the sleeve 22 is about 0.605". The outer diameter of the rotor 10 is about 0.598". The inner diameter of sections 23 and 24 is about 0.375".

To assemble the rotor and motor, the impeller blades 44 are pressed axially into the internal surface of the plastic cylinder 42 with the center hub 38 carried between the impeller blades. With the rotor 10 centered in the sleeve 22 and the supports 27 and 28 inserted into the exterior sections 23 and 24, the inner ends of the sections 23 and 24 are inserted into the outer ends of the sleeve 22 until the studs 35 seat in the recesses 36 of the hub 38.

In the illustrated embodiment, the intermediate pump stator vanes have free edges. It is contemplated that these stator vanes could be encased in a plastic ring, thus providing still another hydrodynamic bearing gap between the plastic ring on the intermediate stator and the plastic cylinder 42 of the rotor 10. It should also be understood that the impeller blades 44 are preferably angulated axially so as to thrust fluid from the inlet to the outlet.

It is also to be understood that, when used as a pump for a heart/lung machine, the plastic housing assembly 21 and all of its components, including the rotor 10, are disposed after use. The stator halves 11a and 11b and the electronic circuit 55 that drives the motor are disconnected from the housing assembly 21 and reused.

FIGS. 2A and 2B show the stator coil windings for two electrical phases designated 13 and 14, respectively, for the stator halves 11a and 11b. Although the windings for each of the two phases 13 and 14 are shown separately, they are physically located on the same laminated core halves 15a and 15b, with phase 14 wound on top of phase 13. FIGS. 2A and 2B schematically depict the locations of slots 61 through 76 in the core halves 15a and 15b through which the electrical conductors are wound. A solid line connecting numbered slots represents a coil of multiple clockwise turns or loops of the electrical conductor, while a dotted line connecting numbered slots represents a coil of multiple counterclockwise turns or loops of the electrical conductor.

Referring to FIG. 2A, to wind phase 13, a first electrical conductor 77 is wound between slots 61 and 63 on stator half 11a in a clockwise direction to form coil 79. The starting point for this phase 13, or the end of conductor 77, is designated by numeral 78 for the purpose of later discussion relating to external electrical connections or hook-ups. Electrical conductor 77 is then wound counterclockwise between slots 63 and 65 to form a coil 80. Winding of conductor 77 continues with a clockwise coil 81 between slots 65 and 67.

A normal motor, i.e., one not split into two halves, would use a counterclockwise winding between slots 67 and 69. The winding would then continue uninterrupted through stator half 11b. However, a coil wound between slots 67 and 69 would span a center plane along which the stator halves 11a and 11b are facially engaged. To accommodate the split stator 11, a shortened coil 82, or short-pitched coil, is wound from slot 67 to slot 68. Because this short pitched coil 82 is counterclockwise, it terminates at slot 67. At slot 67, end or lead 84 of the phase 13 electrical conductor 77 is extended outside stator half 11a for subsequent electrical connection. It should be noted that, as an alternative to short pitched coil 82, the coil between slots 67 and 69 could simply be eliminated. However, the complete elimination of a coil would result in a further loss of performance, and thus is not the preferred embodiment of this invention.

Phase 13 continues on stator half 11b, but the rest of phase 13 is wound with a second electrical conductor 86. End 87 of conductor 86 is wound clockwise between slots 69 and 71, as shown in the left part of FIG. 2A to form coil 88. The windings of phase 13 for stator half 11b continue with counterclockwise coil 89 between slots 71 and 73 and clockwise coil 90 between slots 73 and 75. At slot 75 a standard motor in equilibrium would use a counterclockwise coil between slots 75 and slot 61. However, as indicated previously with respect to stator half 11a, this coil would span the centerline through the stator assembly 11. Thus, a shortened, or short pitched coil 91 is wound between slots 75 and 76, and electrical conductor 86 terminates at slot 75. The end of conductor 86 is designated by numeral 92 for purpose of later discussion related to electrical hook-ups. This ends winding of phase 13. Again, rather than a short pitched coil 92, the coil starting at slot 75 could be eliminated, but this alternative is not presently preferred.

The winding of the phase 14 also uses the short pitched coils and winding of the phase 14 in two separate segments, with subsequent electrical connection outside of the facially engaged stator halves 11a and 11b. As is shown in FIG. 2B, the phase 14 winding in stator half 11a extends from the first end 96 of an electrical conductor 95 and is wound to form a short pitched counterclockwise coil 97 between slots 61 and 62. Electrical conductor 95 continues with alternating clockwise and counterclockwise windings for stator half 11a until slot 68 is reached, with clockwise coil 98 between slots 62 and 64, a counterclockwise coil 99 between slots 64 and 66, and a clockwise coil 100 between slots 66 and 68. Coil 100 terminates at slot 68, and from slot 68 conductor 95 extends from stator half 11a and terminates at end or lead 101.

From the first end 105 another conductor 106, the windings of phase 14 on stator half 11b commence by winding between slots 69 and 70 to form a counterclockwise short pitched coil 107. Phase 14 winding of conductor 106 continues uninterrupted, as depicted schematically in FIG. 2B, with a clockwise coil 108 between slots 70 and 72, a counterclockwise coil 109 between slots 72 and 74 and a clockwise coil 110 between slots 74 and 76. Phase 14 winding terminates at slot 76 and a second end 111 of conductor 106 is extended externally of the stator half to serve as an electrical lead for electrically connecting the stator halves 11a and 11b externally.

FIG. 3 shows the electrical connection scheme for the stator halves. In a normal motor stator that is not split, the electrical connection points brought outside the stator for connection to the driving electronics would consist of the following four connection points: (1) the starting end of phase 13 conductor, designated as RED START, (2) the finish end of the phase 13 conductor, designated as RED FINISH, (3) the starting end of a phase 14 conductor, BLACK START, and (4) the finish end of the phase 14 conductor, BLACK FINISH. Because, each stator, 11a and 11b, half requires two conductors, this invention requires two additional electrical connection points external of the stator. As shown by FIG. 3, to provide continuous electrical conduction of the windings of phase 13, lead 84 is connected to lead 87. To provide continuous electrical conduction of the windings of phase 14, lead 101 is connected to lead 105. The four normal connecting points of RED START, RED FINISH, BLACK START and BLACK FINISH (leads 78, 92, 96 and 111, respectively) are then made in a normal fashion to the electronic circuit 55. The stator 11, rotor 10, circuit 55 and power supply (not shown) forms a brushless DC motor that is operated generally in accordance with the principles described in U.S. Pat. Nos. 4,027,215, 4,238,717 and 4,492,903 each of which is incorporated by reference herein in its entirety.

In the above described winding procedure, FIGS. 2A and 2B depict four clockwise coils per phase, and thus the back EMF generates, by motor action, within the four coils, the same voltage at the same time. Another four coils per phase are wound counterclockwise with opposite orientation. The back EMF voltage in these four counterclockwise coils is the same as that generated in the four clockwise coils. Hence, the voltages for all eight coils, though changing sinusoidally, are in phase with each other at all times. These eight coils correspond to the 8 magnetic poles in rotor 10. Four coils at any time are north driven poles and four coils at any time are south driven poles. Thus, the stator assembly 11 depicted in FIGS. 2A and 2B is designated as a 2 phase, 16 slot, 8 pole motor.

In comparing the expected drop in performance of the split stator assembly 11 to a conventional motor stator, one must consider the short pitched coils as a performance loss. Since there are two short pitched or half coils out of a possible eight per phase, as compared to a conventional motor stator, the theoretical performance loss is calculated to be $2 \times \frac{1}{2} = 1$ out of eight total, or a 12.5 percent loss. Actual measured stall torque loss is about 16–20%.

In general, selection of a greater number of slots should lead to a smaller calculated loss of performance. For example, a 2 phase, 32 slot, 8 pole motor would have a slightly lower theoretically calculated loss of performance of about 10.4 percent. However, the ratio of slots to poles can also critically affect the calculated loss when configured as a split motor stator. For example, a 2 phase, 24 slot, 4 pole motor would yield a theoretical 35 percent loss. These examples are included to point out that the thrust of the invention is directed toward a split stator, and that the invention is not limited to the number of poles, slots, or phases depicted in FIGS. 2A and 2B.

It is possible that the short pitched coils may produce some perturbations in the rotor rotation, resulting in turbulence in the pumping of liquid. These perturbations and the performance loss of this split stator motor are generally due to the lower amount of flux generated by the short pitched coils and the discontinuities in magnetic flux across the center plane. To compensate for this reduced magnetic flux, the short pitched coils could be wound with a finer conductor to form a short pitched coil with twice as many turns as the other standard or full pitched coils. Because magnetic flux is determined by ampere-turns, and this modification would double the number of turns, this modification would result in the short pitched coils generating about the same magnetic flux as the other coils, assuming non-magnetic saturation of the tooth about which the winding is made. However, the finer wire and the additional conductor length required by this embodiment would increase the total resistance of the coil and result in less current through all of the windings for that electrical phase.

As another alternative, one additional conductor could be wound alongside each of the short pitched coils to form another short pitched coil. An additional, correctly timed current pulse through these additional short pitched coils would effectively double the total current through both short pitched coils, thereby generating a total magnetic flux substantially equal to the magnetic flux generated by the other coils.

FIG. 1, 4 and 5 show the details of the mechanical connection scheme used to connect the stator halves 11a and 11b. FIG. 4 shows the disconnected stator halves 11a and 11b on opposite sides of the plastic housing 21 and tubes 112 and 113 connected to the ends of housing 21 to form a blood flow path 114. The ends or leads of each of the conductors extend to one end of the respective, epoxy-encapsulated stator halves 11a or 11b, and they are fed to a respective cable 116a or 116b that connects the windings to the other of the stator halves or to circuit 55 (FIG. 1).

Two spaced radial grooves 118 are formed in each stator half, 11a and 11b, for mechanical connection to the housing 21. The depth of the grooves 118 is chosen so as to avoid impinging on the routing path of the leads or cables, 116a and/or 116b. Two cam followers 120 in the form of pins 120 are embedded in each stator half, with each pin 120 extending across a respective groove 118 a predetermined distance from the bottom thereof.

Housing 21 includes a pair of spaced mounting components 121 integrally formed thereon. The mounting components 121 serve as cammed bearing surfaces for connecting the stator halves 11a and 11b to housing 21. The mounting components 121 on the housing 21 are placed into the grooves 118 of one stator half, 11a or 11b, so that the pins 120 are in contact with a pair of spaced declined cam surfaces 124 facing radially outwardly from housing 21 in a first direction. The other stator half is then placed over the housing 21 and facially engages the other stator half such that its pins 118 are also in contact with a pair of spaced declined cam surfaces 124 facing radially outwardly from housing 21 in an opposite, second radial direction, opposite the first direction. By grasping either one of a pair of knobs, 132 or 133, which are preferably formed integrally on the ends of the housing 21, the stator halves 11a and 11b are rotated with respect to the housing 21, and the pins 120 of both stator halves 11a and 11b move along the declined cam surfaces 124 until the pins 120 positively lock into the cam ends 135. The magnetic attraction between the magnets of the rotor 10 located inside the housing 21 and the iron in the stator halves 11a and 11b also pulls the two stator halves 11a and 11b together around the housing 21.

To separate the components, the stator halves 11a and 11b are rotated in the opposite direction with respect to housing 21 to rotate the pins 120 out of the cam ends 135. As the pins 120 move along the now-inclined cam surfaces 124, away from cam ends 135, the stator halves 11a and 11b are pushed apart in spite of the magnetic attraction between the rotor magnets within the housing 21 and the iron of the stator 11. Notches 137 in the outer surface of the stator halves 11a and 11b permit the operator to grasp one of the stator halves and remove it from the other. The housing 21 is then readily removed from the other of the stator halves.

In the operation of the invention, the motor is connected to the patient's circulatory system, either externally or internally. A power supply (not shown) and the electronic circuit 55 actuate the motor stator 11 to rotatably drive the rotor. The impeller blades on the rotor drive blood axially through the center of the motor, thereby substituting for or assisting the heart and maintaining the patient's needed circulation. The action of the impeller blades creates a high pressure at the outlet end of the rotor and a lower pressure at the inlet end of the rotor. That high pressure causes leakage flow of blood through the gaps 50 and 51. It is calculated that the residence time of a cell in the gap 50 is about 0.034 seconds, and the residence time of a cell in each gap 51 is about 0.013 seconds. The shear stress in the gap 50 is about 1900 dynes per square centimeter, and the shear stress in the gap 51 is about 2200 dynes per square centimeter.

The invention has been described in connection with a two-stage pump, that is, a pump having two stages of impeller blades. To handle larger loads and to operate at a lower speed, the principles of the invention may be embodied in a three-stage pump wherein the rotor carries three stages of impeller blades. While this motor/blood pump has been operated at rotary speeds of 16,500, it is applicant's belief that the preferred rotary speed for the two-stage motor/pump is about 13,500 rpm. The preferred speed for a three-stage motor/pump is about 12,700 rpm. The motor should pump about 6 liters per minute at about 300 mmHg of pressure.

In the described application of the invention, one or more pumps are connected external to the body to perform heart/lung bypass for a heart/lung machine. It is also contemplated that the pump be inserted in a femoral artery and femoral vein in the leg. When it is implanted, the pump can be an implantable assist device or total artificial heart.

Aside from pump applications, the split motor concept can be used, for example, with two phase and three phase induction and synchronous motors, hysteresis synchronous motors, stepper motors, and resolvers. Utilizing this invention, any alternating current or brushless d.c. machine can be split. With this in mind, and with the general explanation of configurational problems that lead to the need for a split motor in mind, coupled with the particular application of axial flow pumps, it should be readily understood that the applications for a split motor and the motivations for its use are many and varied.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof.

We claim:

1. A motor/blood pump combination comprising:
   an axial flow blood pump including a cylindrical housing;
   a motor to drive the pump, the motor including a pair of stator halves surrounding and mechanically connectable to the housing to form a stator for driving the pump; and
   a rotor located within the housing and rotatably driven by the stator, the rotor being rotatable within the housing on a hydrodynamic bearing, whereby the pump is easily removable from the housing by separating the stator halves.

2. The motor/blood pump of claim 1 wherein each stator half has a predetermined number of slots and further comprises:
   at least one conductor wound on the slots to form a plurality of coils, one of the coils being short pitched so as to span only half as many slots as the other coils.

3. The motor/blood pump of claim 2 wherein the stator halves are connectable along a center plane and each short pitched coil is located in a slot adjacent the center plane.

4. The motor/blood pump of claim 3 wherein each stator half further comprises:

two conductors wound on the slots to form a first plurality of coils for a first phase and a second plurality of coils for a second electrical phase, each phase having a short pitched coil, and the short pitched coils of the first and second phases located at opposite end slots.

5. The motor/blood pump of claim 2 wherein each short pitched coil has about twice as many turns as the other coils formed by the respective conductor, thereby to generate magnetic flux at the short pitched coils that is substantially equal to the magnetic flux generated by the other coils.

6. The motor/blood pump of claim 2 and further comprising:
   an additional conductor for each short pitched coil, each of said additional conductors being wound around the slots where a short pitched coil is located and each said additional coil being electrically connected to a power source in parallel with the respective short pitched coil, thereby to generate additional magnetic flux at the short pitched coils, so that the magnetic flux at the short pitched coils is substantially equal to the magnetic flux generated by the other coils.

7. The motor/blood pump of claim 1 and further comprising:
   a cylindrical housing;
   a pair of spaced cam bearing located on the housing; and
   each stator half further including a correspondingly spaced pair of cam followers adapted to coact with the spaced cam bearings to rotatably connect/disconnect the respective stator half to/from the housing.

8. The motor/blood pump of claim 7 wherein each cam follower further comprises:
   a pin located within a radial groove int he respective stator half.

9. The motor/blood pump of claim 7 wherein the housing further comprises:
   a pair of spaced knobs located outside of the cam bearings, the knobs facilitating rotatable connection and disconnection of the stator halves from the housing.

10. The motor/blood pump of claim 9 wherein one of the knobs is smaller than the other of the knobs so as not to interfere with electrical leads extending outwardly from the stator halves.

11. A motor/blood pump combination for pumping blood and a blood compatible liquid through a conduit connected between a patient and a heart/lung machine:
    a cylindrical axial pump housing connectable along the conduit to pump blood and blood compatible liquid therethrough;
    a rotor assembly located inside the housing, the rotor assembly being rotatable within the housing on a hydrodynamic bearing, the rotor assembly including at least one impeller blade adapted to pump blood and/or blood compatible liquid through the housing during rotation;
    a pair of stator halves mechanically connected to the housing to form a stator assembly thereabout and the stator halves electrically connected to each other outside of the stator assembly, wherein the stator halves are mechanically connected along a midplane which longitudinally divides the pump housing and each of the stator halves has a plurality of windings, each of the windings located entirely on one side of the midplane; and
    control means electrically connected to both stator halves to electrically actuate the stator halves to rotatably drive the rotor assembly to pump blood and/or blood compatible fluid through the conduit.

12. The motor/blood pump combination of claim 12 wherein the rotor assembly has two sets of axially spaced impeller blades and the pump housing has three stages of pump stator blades.

13. A motor/blood pump combination for pumping blood along a blood flow path comprising:
    a cylindrical pump housing located along the blood flow path;
    at least one set of pump stator blades fixedly mounted within the housing;
    a rotor held axially within the housing and rotatable within the housing on a hydrodynamic bearing when a magnetic field is applied within the hosing;
    at least one set of impeller blades connected to the rotor and adapted to coact with the stator blades to pump blood from an inlet of the housing toward an outlet of the housing when the rotor is rotated;
    a pair of stator halves mechanically connected to the housing to form a housing assembly in radial alignment with the rotor, the stator halves being electrically connected exterior of the stator assembly and adapted to create a varying magnetic field within the housing to drive the rotor, wherein the stator halves are mechanically connected along a midplane which longitudinally divides the pump housing and each of the stator halves has a plurality of windings, each of the windings located entirely on one side of the midplane; and
    a controller electrically connected to the stator halves and adapted to electrically actuate the stator halves to drive the rotor at a predetermined rotary speed to pump blood through the housing at a flow rate of about six liters per minute and at a pressure of about 300 mmHg of pressure.

14. A motor/pump combination comprising:
    a cylindrical pump housing;
    a rotor located inside the housing, the rotor being rotatable within the housing while supported on a hydrodynamic bearing therebetween;
    at least one impeller blade connected to the rotor and rotatable therewith;
    a stator assembly of at least two stator sections mechanically connected to the housing, wherein the stator sections are mechanically connected along a midplane which longitudinally divides the pump and each of the stator sections has a plurality of windings, each of the windings located entirely on one side of the midplane; and
    control means electrically connected to each stator section and adapted to electrically actuate the stator sections to drivably rotate the rotor and said at least one impeller blade, thereby to pump liquid through the housing.

15. The motor/pump combination of claim 14 wherein said stator assembly consists of two stator halves.

16. The motor/pump combination of claim 14 wherein each stator section further comprises:
    at least one electrical conductor wound on the respective section to form a predetermined number of coils, one of the coils being short pitched with respect to the other coils.

17. The motor/pump combination of claim 14 wherein the stator assembly consists of two stator halves facially engaged along a center plane through the housing, each stator half having at least one electrical conductor wound on the respective section to form a predetermined number of coils, one of the coils being short pitched with respect to the other coils, each short pitched coil of a respective stator half located adjacent the center plane.

18. The motor/pump combination of claim 14 wherein each stator section further comprises:
    two electrical conductors wound on each stator section through slots spaced equidistantly around the stator and forming a semi-circle, each electrical conductor having one short pitched coil, the short pitched coils located at opposite ends of the semi-circle.

19. The motor/pump combination of claim 15 and further comprising:

a pair of spaced cam bearing located on the cylindrical housing, each cam bearing including a pair of declined cam surfaces and cam ends spaced 180° apart; and each stator section further comprising a corresponding pair of spaced cam followers adapted to coact with the spaced cam bearings to positively lock to the housing.

20. A motor comprising:
a rotor;
sleeve means circumscribing the rotor;
a pair of spaced cam bearings carried by the sleeve means; and
a stator assembly with a bore therethrough, the bore being sized to circumscribe the sleeve means, the stator assembly further including two stator halves mechanically connected to the cam bearings, the stator assembly adapted to rotatably drive the rotor.

* * * * *